(12) United States Patent
Franciosa

(10) Patent No.: US 12,178,734 B2
(45) Date of Patent: Dec. 31, 2024

(54) MULTI-MATERIAL WEIGHTLIFTING BELT WITH FITMENT GUIDING RAMP

(71) Applicant: ELEMENT 26 LLC

(72) Inventor: Jason T. Franciosa, Port St. Lucie, FL (US)

(73) Assignee: Element 26 LLC, Fort Pierce, FL (US)

( * ) Notice: Subject to any disclaimer, the term of this patent is extended or adjusted under 35 U.S.C. 154(b) by 120 days.

(21) Appl. No.: 18/156,163

(22) Filed: Jan. 18, 2023

(65) Prior Publication Data

US 2023/0404788 A1 Dec. 21, 2023

Related U.S. Application Data

(60) Provisional application No. 63/366,631, filed on Jun. 18, 2022.

(51) Int. Cl.
*A61F 5/02* (2006.01)

(52) U.S. Cl.
CPC .................... *A61F 5/028* (2013.01)

(58) Field of Classification Search
CPC ...... A61F 5/3738; A61F 5/0102; A61F 5/012; A61F 5/34; A61F 5/055; A61F 5/0193; A61F 5/03; A61B 17/1327; A61B 17/1325; A61B 17/135; A61B 17/1322; A61B 2017/00557; A61B 2017/00548

See application file for complete search history.

(56) References Cited

U.S. PATENT DOCUMENTS

| | | | | |
|---|---|---|---|---|
| 5,316,022 A | * | 5/1994 | Schiek, Sr. | A61F 5/028 2/338 |
| 5,407,422 A | * | 4/1995 | Matthijs | A61F 5/0193 2/338 |
| 5,500,959 A | * | 3/1996 | Yewer, Jr. | A61F 5/028 2/322 |
| 8,591,445 B2 | * | 11/2013 | Serola | A61F 5/028 602/5 |
| 2016/0332027 A1 | * | 11/2016 | Matthews | A63B 21/0442 |

* cited by examiner

*Primary Examiner* — Loan B Jimenez
*Assistant Examiner* — Andrew M Kobylarz
(74) *Attorney, Agent, or Firm* — Christensen, Fonder, Dardi & Herbert PLLC; John P. Fonder

(57) ABSTRACT

A lifting belt for fitment on a torso of a user, including: a primary support portion having a first end with a first end face and a second end, an inner side and outer side; a buckle connected to the primary support portion; and a strap portion including: a main portion having a cinching portion configured to engage with the buckle for adjusting fitment of the lifting belt; and a guiding ramp portion having a first end connected to the cinching portion and a second end connected to the inner side of the primary support portion, thereby forming a guiding ramp between the inner side of the cinching strap portion and the inner side of the primary support portion such that the first end is guided along the guiding ramp portion and over the second end when the lifting belt is fitted to the torso of the user.

19 Claims, 13 Drawing Sheets

MULTI-MATERIAL WEIGHTLIFTING BELT WITH FITMENT GUIDING RAMP

RELATED APPLICATIONS

This patent application claims the benefit of U.S. Provisional Application No. 63/366,631, filed Jun. 18, 2022, the disclosure of which is incorporated by reference in its entirety.

FIELD OF THE INVENTION

The present invention is directed to weightlifting belts, and in particular, lifting belts with features facilitating rapid and unencumbered securement to a user.

BACKGROUND

Current leather weightlifting belts are bulky and cumbersome, requiring athletes to fasten the belt by a steel lever or steel pin setup. This type of belt inhibits Olympic Weightlifting because of the bulky locking mechanism placed on the front of the body that inhibits the barbell path. If the barbell hits the locking buckle, the lift is missed and can lead to an injured lifter. Additionally, using a steel pin buckle is slow to adjust. Nylon weightlifting belts do not provide the structural support for lifters lifting heavy loads, and this type of belt relies simply on hook-and-loop fastening to secure the belt. Over time, hook-and-loop structures wear out and result in failure of the belt's efficacy. As can be seen, there is a need for an improved weight-lifting belt.

SUMMARY

Embodiments of the claimed weightlifting belt may be used by athletes requiring core and back support during weightlifting. Unique to embodiments of the weightlifting belt is a combination of two traditional belt methodologies and materials, as well as a guide ramp device that allows the ends of the belt to overlap without interference during adjustment. The weightlifting belt of the present disclosure is easily and rapidly adjusted, can be worn during all lifting, and provides more support than known nylon belts.

Embodiments of the present disclosure include a lifting belt for fitment on a torso of a user, that comprises a primary support portion defining a first width and first thickness and including a first end with a first end face a second end with a second end face, an inner side and an outer side; a fastening assembly connected to the primary support portion; and a strap portion including: a main portion having an attached portion attached to the primary support portion and a cinching portion configured to engage with the fastening assembly for securing and adjusting fitment of the lifting belt, the cinching portion connected to the primary support portion and extending from the second end of the primary support portion, the cinching portion defining a second width and a second thickness; and a guiding ramp portion having a first end connected to the cinching portion and a second end connected to the inner side of the primary support portion, thereby forming a guiding ramp between the inner side of the cinching strap portion and the inner side of the primary support portion such that the first end is guided along the guiding ramp portion and over the second end when the lifting belt is fitted to the torso of the user.

In an embodiment, the primary support portion comprises a leather material, and the cinching portion of the strap portion comprises a nylon material, and the first thickness of the primary support portion is greater than the second thickness of the cinching portion.

In an embodiment, the guiding ramp portion forms an angle with a lengthwise axis of the primary support portion in a range of 10° to 60° when the guiding ramp portion is subjected to a pulling force along the lengthwise axis. In another embodiment, the angle is in a range of 15° to 45°.

In an embodiment, the guiding ramp portion defines a length that is less than the second length of the cinching portion.

In an embodiment, the guiding ramp portion defines a third width that is less than the first width of the primary support portion. In one such embodiment, the third width of the guiding ramp portion is substantially the same as the second width of the cinching portion.

In an embodiment, an end face width of the first end face is substantially equal to the first thickness of the primary support portion and is greater than the second thickness of the cinching portion. In one such embodiment, the primary support portion comprises leather, the cinching portion and the guiding ramp portion comprise a polymer material, the cinching portion is sewn to the outer side of the primary support portion at the second end and the guiding ramp portion is sewn to the inner side of the primary support portion.

In an embodiment, the lifting belt also includes a hook portion on an attached portion of the strap portion facing outwardly from the outer side of the primary support portion and a loop portion configured to engage with the hook portion, the loop portion attached to an end of the cinching portion.

In an embodiment, the fastening assembly comprises a buckle assembly with a buckle frame, sliding pin and rotating cylinder.

Embodiments also include a method of fitting the lifting belt of claim 1 onto a torso of a user, comprising the steps of: wrapping lifting belt on the torso of the user such that the inner side of the primary support portion is adjacent to the torso, causing the primary support portion to form an open loop shape; threading an end of the cinching portion through the fastening assembly; pulling the end of the cinching portion, causing the first and second ends of the support portion to move towards one another; pulling the end of the cinching portion, causing the first end to engage with the guiding ramp portion, and to engagably slide along an outer side of the guiding ramp portion until the first end moves past the second end, such that the first end face and the second end face do not contact one another, and end portions of primary support portion overlap.

One such method also includes placing the cinching portion against an attached portion of the strap portion, causing a hook portion on the primary support portion to engage with a loop portion on the cinching portion of the strap portion, thereby connecting the cinching portion to the attached portion and the primary support portion.

Another embodiment of the lifting belt comprises: a leather primary support portion defining a first width and first thickness and including a first end with a first end face defining a first end-face width, a second end with a second end face, an inner side and an outer side, the first thickness being in a range of 2 mm to 12 mm and the first end-face width being in a range of 2 mm to 12 mm; a buckle assembly connected to the primary support portion; and a strap portion including: a main portion having an attached portion attached to the primary support portion and a non-leather cinching portion configured to engage with the buckle for securing and adjusting fitment of the lifting belt, the non-leather cinching portion sewn to the outer side of the leather primary support portion and extending from the second end of the leather primary support portion, the non-leather cinching portion defining a second width that is less than the first width of the leather primary support portion, and a second thickness that is less than the first thickness of the leather primary support portion; and a guiding ramp portion having a first end connected to the cinching portion and a second end sewn to the inner side of the leather primary support portion, thereby forming a guiding ramp between the inner side of the non-leather cinching strap portion and the inner side of the leather primary support portion such that the first end of the leather primary support portion is guided along the guiding ramp portion and over the second end of the non-leather primary support portion when the lifting belt is fitted to the torso of the user. In one such embodiment, the non-leather cinching portion comprises a nylon cinching portion and the guiding ramp portion comprises a nylon material.

In an embodiment, the guiding ramp portion forms an angle with a lengthwise axis of the leather primary support portion in a range of 10° to 60° when the guiding ramp portion is subjected to a pulling force along the lengthwise axis. In another embodiment, the angle is in a range of 15° to 45°.

In an embodiment, a length of the guiding ramp portion is greater than the first thickness of the leather primary support portion and less than a length of the cinching portion.

In an embodiment, a width of the guiding ramp portion is less than the second width of the leather primary support portion.

The various embodiments of the disclosure are described below with respect to the figures.

BRIEF DESCRIPTION OF THE FIGURES

The drawings included in the present patent application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
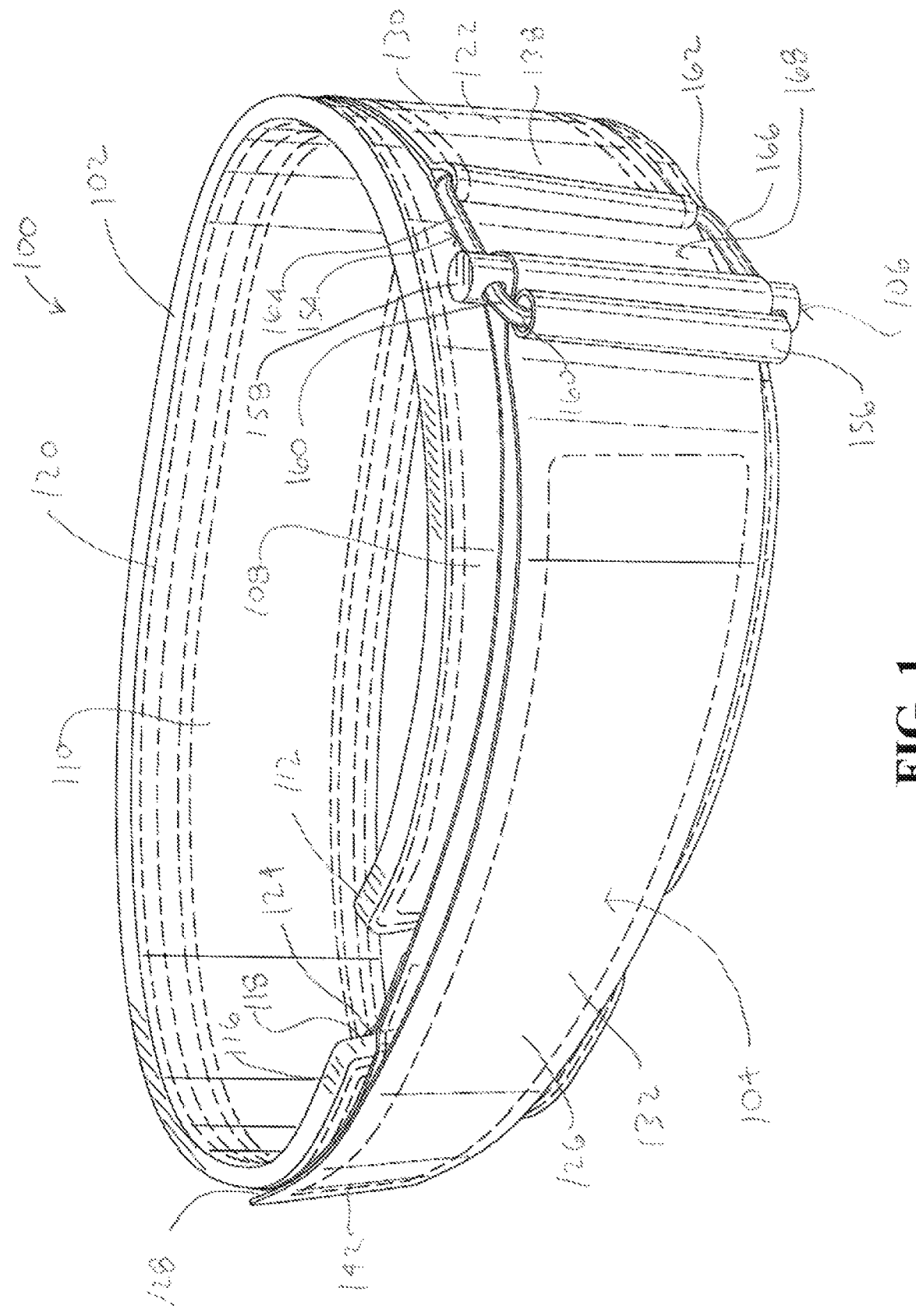
FIG. 1 is a perspective view of the lifting belt in a first buckled configuration, according to an embodiment of the disclosure.

While the embodiments of the disclosure are amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

Figure 2:
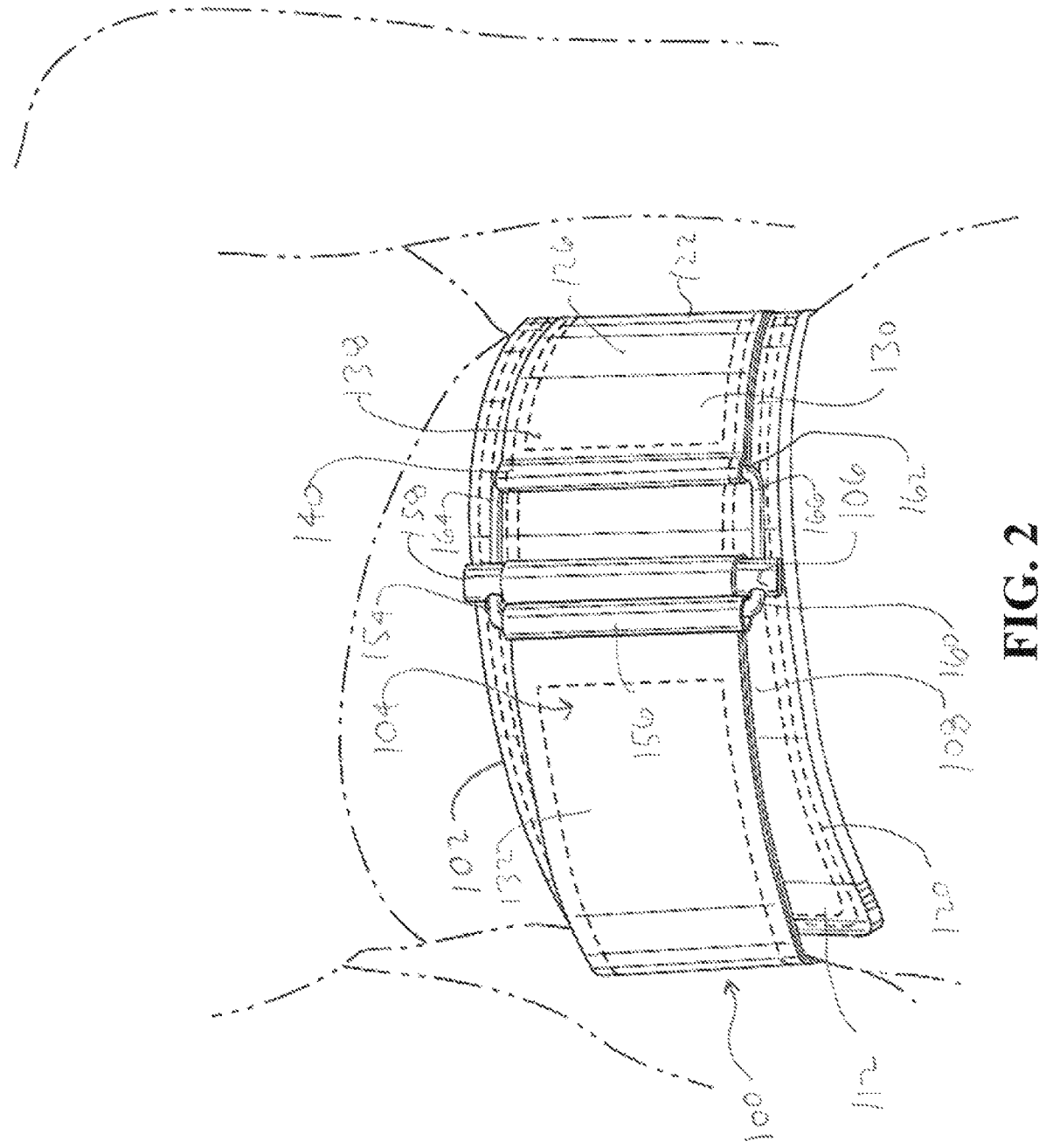
FIG. 2 is another perspective view of the lifting belt of FIG. 1 in a buckled configuration as worn by a user, according to an embodiment of the disclosure.

Referring to FIG. 1, an embodiment of a multi-material weightlifting belt 100 with ramped adjustability ("lifting belt") is depicted in a first buckled or fastened configuration. Referring also to FIG. 2, and as will be described further below, lifting belt 100 is configured to be worn by a user, such that lifting belt 100 is tightly wrapped about a torso of the user, exerting pressure on, and providing support to, muscles of the torso, including the back and abdomen. When the user lifts a relatively heavy load, such as weights for exercise or competition, lifting belt 100 can lower stress on the lower back and potentially prevent injuries during lifting of the load.

Known lifting belts can be difficult to adjust when fitting or attaching to the torso, in part due to the characteristics of the stiff, yet supportive, leather components of such known belts. Embodiments of the disclosure described herein include features for easing fitment of a lifting belt by a user of the belt.

Referring to FIGS. 1 through 9, details of an embodiment of lifting belt 100 are depicted. In the depicted embodiment, lifting belt 100 includes primary support portion 102, strap portion 104 and buckle assembly 106.

In an embodiment, primary support portion 102 includes first, front or outer side 108, second, back or inner side 110, first end 112 with first end face 114, second end 116 with end face 118 and optional decorative stitching 120. Primary support portion 102 has a length L1 along a lengthwise axis $A_L$ (see FIG. 3), a width W1 along widthwise axis $A_W$ (see FIG. 3) and thickness T1 (see FIG. 3).

Primary support portion 102 may be relatively flexible along its length L1 about a lengthwise axis $A_L$ such that primary support portion 102 may be wrapped about the torso of the user in a loop or circle shape. On the other hand, primary support portion 102 but may be relatively inflexible or rigid about its width W1 or widthwise axis W1 so as to provide maximum support. To accomplish this balance, the width of primary support portion 102 will generally be less than length L1. Thickness T1, in an embodiment, and depending on material used, may be relatively thick to not only provide sufficient support and strength, but to also maintain sufficient widthwise rigidity.

In an embodiment, length L1 is longer than width W1, and primary support portion 102 is generally rectangular in shape, forming a belt-like portion.

In an embodiment, primary support portion 102 with thickness T1 comprises a first relatively thick, natural material, such as leather. In other embodiments, primary support material 102 may comprise other natural materials, or may comprise synthetic materials. In an embodiment, a material of primary support portion 102 comprises a polymer material. In one such embodiment, the polymer material is a faux leather material.

In an embodiment, primary support portion 102 is made from a material having a first Young's modulus in a range of 20 to 100 N/mm². In one such embodiment, the material is a natural leather material derived from the hide of an animal, such as, but no limited to, cowhide.

In an embodiment, thickness T1 is in a range of 2 mm to 12 mm. In an embodiment, thickness T1 is in a range of 4 mm to 6 mm, which provides the benefit of sufficient strength, flexibility, and ability to slide over guiding-ramp portion 124, as described further below. As will become evident from the further description below, a greater thickness in a traditional lifting belt can cause interference of belt ends when fitting and adjusting the lifting belt. However, and as also described further below, lifting belt 100 with its unique ramp end-interface structure can be easily adjusted, without end-to-end interference, even for belts 100 having relatively large thicknesses T1.

In an embodiment, primary support portion 102 comprises a single layer. In other embodiments, primary support portion 102 comprises multiple layers, some of those layers comprising different layer materials or different layer thicknesses.

Outer side 108 is configured to face away from a user wearing lifting belt 100, while inner side 110 is configured to be in contact with the torso of the user. In an embodiment, one or both of sides 108 and 110 may be treated. In an embodiment, inner side 110 has a different treatment as compared to outer side 108. In one such embodiment, inner side 110 has a rough, grippable surface, while outer side 108 is treated such that the outer surface is smooth. In one such embodiment, inner side 110 is a suede finish, which has a somewhat rough texture for improved grip with the user's torso, while outer side 108 is a smooth, in some cases hardened surface. Such an embodiment assist with lifting belt 100 staying in position on the user, minimizing slippage, and at the same time, reduces unwanted friction between outer side 108 and any object moving along it surface, e.g., a barbell.

First end face 114 is at first end 112 of primary support portion 102, while second end face 118 is at second end 116 of primary support portion 102, such that the two end faces are on opposite ends of the primary support portion 102. In an embodiment, each end face 114, 116 is generally planar, as depicted, and extending transversely to inner side 108 and outer side 110. In an embodiment, end faces 114, 116 each extend substantially perpendicularly to inner side 108 and outer side 110. In an embodiment, an end face length of one or both of end faces 114, 116 is substantially equal to a width of primary support portion 102, and an end face width of one or both of end faces 114, 116 is substantially equal to thickness T1 of primary support portion 102.

In an embodiment, primary support portion 102 may include stitching 120. Stitching 120 may be for decorative purposes, but may also serve the function of connecting multiple layers of material of primary support portion 102 in the case of a multi-layer primary support portion 102.

Strap portion 104, in an embodiment comprises first or main portion 122 and second or guiding-ramp portion 124.

Main portion 122 is attached to primary support portion 102, extends along lengthwise axis $A_L$, and has a length L2 and a width W2. As depicted, and in an embodiment, length L2 is greater than width W2, and thickness T2 is less than thickness T1. As such main portion 122 forms a thin belt-like structure. In an embodiment, width W2 is less than width W1 of primary support portion 102, and thickness T2 is less than thickness T1 of primary support portion 102. In an embodiment, thickness T2 is in a range of 0.5 mm to 5.0 mm; in another embodiment, thickness T2 is in a range of 1.0 mm to 1.5 mm. A thickness in a range of 1.0 mm to 1.5 mm, in combination with materials described below provide a benefit of sufficient strength, flexibility, and manufacturability (e.g., sewing onto primary support portion 102).

In an embodiment, main portion 122 may comprise any of a variety of materials, including naturally occurring materials or synthetic materials. Naturally-occurring materials may include cotton, leather, and so on. Synthetic materials may include a polymer such as nylon or nylon blended with other polymer materials. In an embodiment, main portion 122 may comprise a woven belt structure.

In an embodiment, a material of main portion 122 may be less elastic than the material of primary support portion 102. In one such embodiment, a Young's modulus of main portion 122 may be less than a Young's modulus of primary support portion 102.

Main portion 122 includes first, outer or top side 126, second, inner or bottom side 128, attached overlapping portion 130, extending, detached cinching portion 132, optional hook portion 134 and optional loop portion 136.

Attached overlapping portion 130 is attached to primary support portion 102, such that inner side 128 contacts outer side 110 of primary support portion 102. Attached portion 130 may, in an embodiment, be sewn onto primary support portion 102. Attached overlapping portion 130 includes first end portion 138, which is attached to outer side 110 of primary support portion 108, such that first end portion 138 is proximal to first end 112 of primary support portion 102 and proximal to buckle or fastening assembly 106.

In an embodiment, first end portion 138 of attached overlapping portion 130 forms a sleeve or channel 140 which receives a portion of buckle 106, as described further below.

Figure 10:
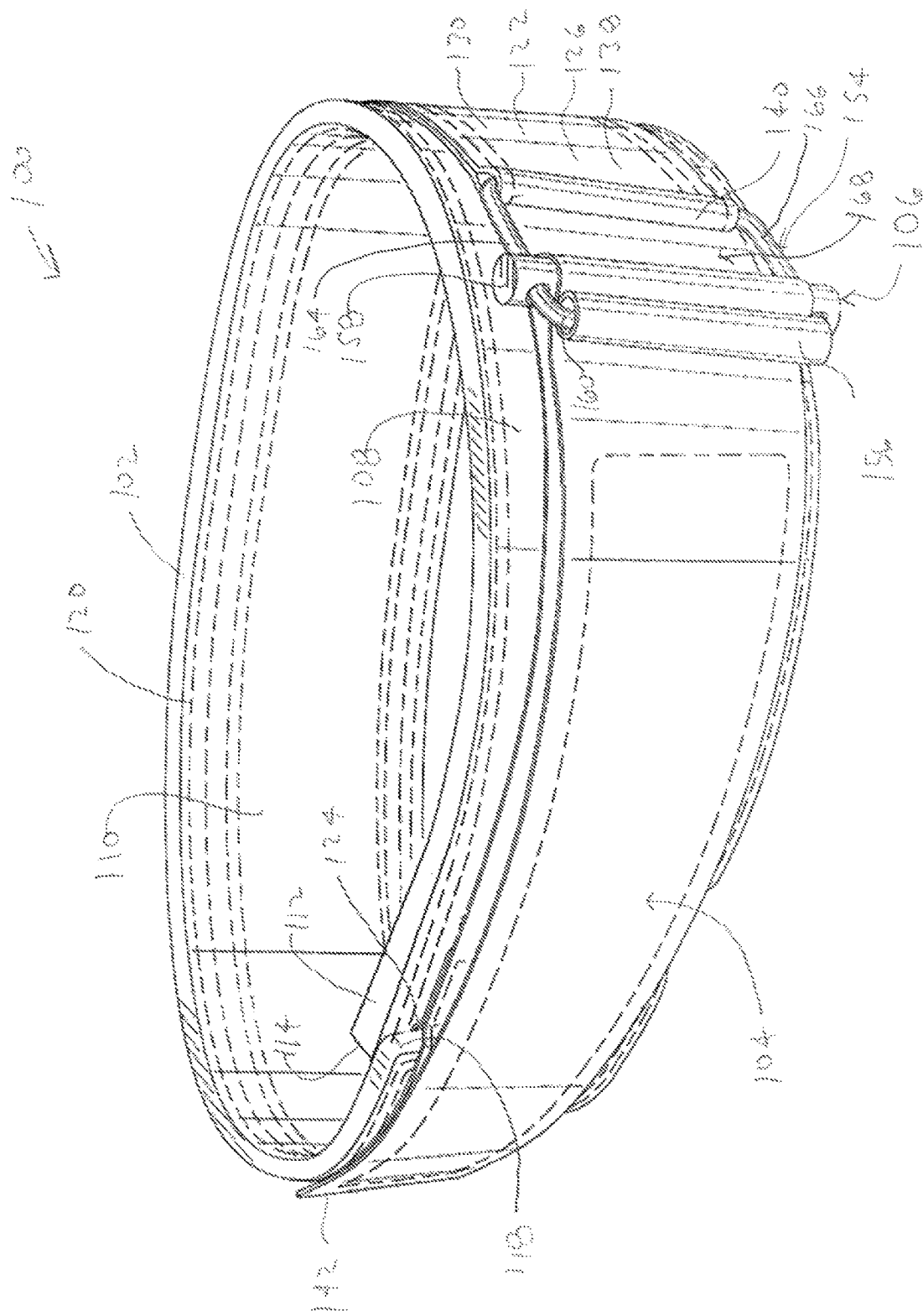
FIG. 10 is a perspective view of the lifting belt in a second buckled configuration, according to an embodiment of the disclosure.

First end portion 138 is located a distance or offset "O" from first end 112 and its end face 114. As explained further below, offset O defines a maximum length of primary support portion 102 where a length of primary support portion 102 near first end 112 can overlap a length of primary support portion 102 near second end 116, when lifting belt 100 is in a buckled configuration, such as depicted in FIG. 10. In an embodiment, offset "O" is in a range of 2" to 12"; in another embodiment, offset "O" is in a range of 4" to 10"; in another embodiment, offset O is in a range of 6" to 8". If offset "O" is too short, lifting belt 100 is more limited in how small of a loop can be formed, and when offset "O" is too long, it may be cumbersome to adjust.

Still referring to FIGS. 1-9, cinching portion 132 is not attached to primary support portion 102, extends from second end 116 of primary support portion 102, and includes second end 142.

In an embodiment, main portion 122 of strap portion 104 includes hook portion 134 attached to outer side 126 on attached portion 130. Main portion 122 of strap portion 104 may also include a corresponding loop portion 136 also attached to outer side 126 on cinching portion 132. Hook portion 134 and loop portion 136 together form a hook-and-loop structure wherein hook portion 134 attaches to loop portion 136 when portions 134 and 136 are pressed together, such as when cinching portion 132 is folded over onto attached portion 130 to secure lifting belt 100 around the torso of a user.

Figure 11:
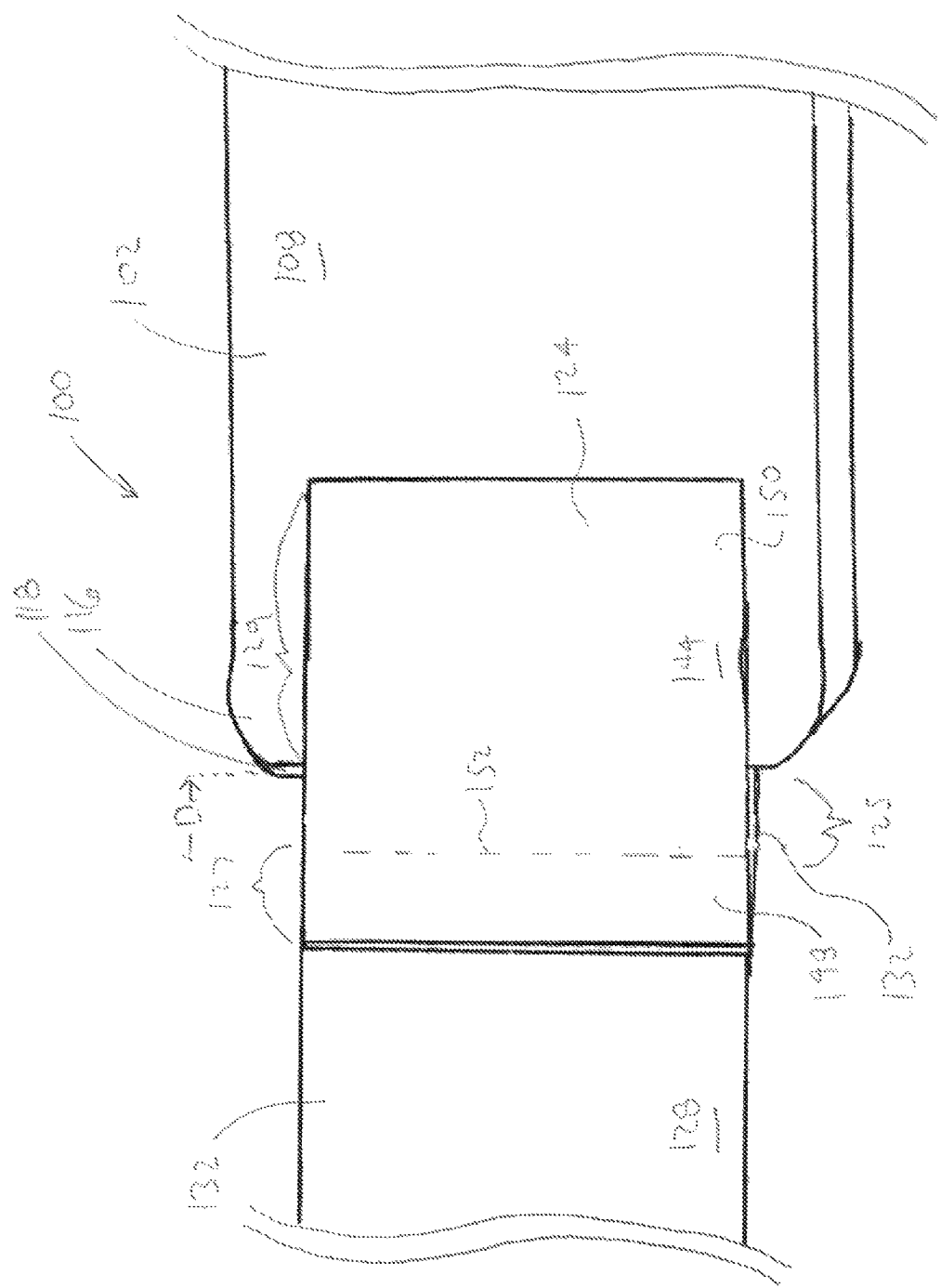
FIG. 11 is a view of an inner side of the lifting belt depicting a guiding-ramp portion, according to an embodiment of the disclosure.

Referring also to FIG. 11, guiding-ramp portion 124 includes angled transition portion 125, first or inner side 144, second or outer side 146, first end 148 and second end 150.

Guiding-ramp portion 124 extends lengthwise along axis $A_L$ with a length L3, and extends widthwise along axis $W_L$ with a length W3. In an embodiment, length L3 is less than, and in some case significantly less than length L2 of main portion 122; width W3 may be substantially the same width as width W2 of main portion 122.

In an embodiment, guiding-ramp portion 124 comprises the same material as main portion 122.

First end 148 of guiding-ramp portion 124 is attached to main portion 122 of strap portion 104, such that outer side 146 is attached and adjacent to inner side 128 of main portion 122 of strap portion 104, at point of attachment 152. Point of attachment 152 is located a distance D from second end face 118 of second end face 116. Point of attachment 152 may comprise a continuous attachment area, line or seam extending all or portions of width W3 or W2, attaching guiding-ramp portion 124 to main portion 122. Distance D is defined as the distance from end face 118 to the closest part of the point of attachment 152.

Second end 150 of guiding ramp 124 is attached to inner side 108 of primary support portion 102 at a location near to second end 116 and end face 118. Outer side 146 is adjacent to and in contact with inner side 108.

Figure 14:
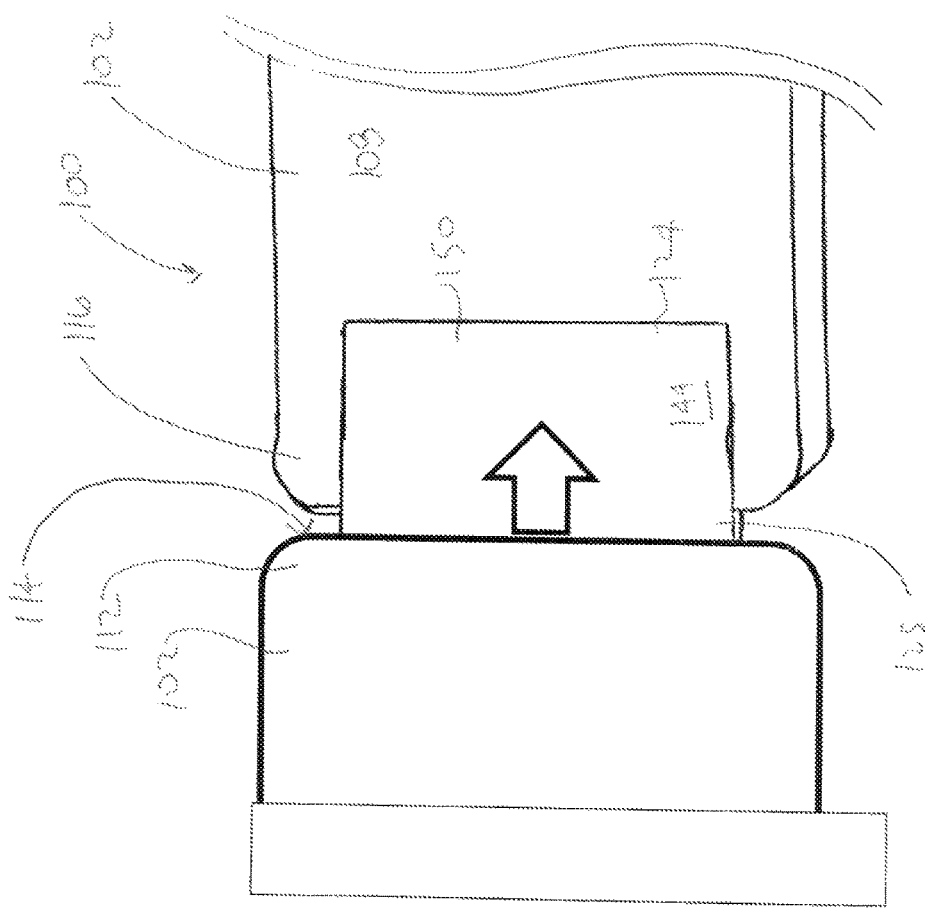
FIG. 14 is a view of an inner side of the lifting belt depicting an end of the primary support portion engaging a guiding ramp portion, according to an embodiment of the disclosure.

Referring also to FIG. 14, guiding-ramp portion 124 forms angled transition portion 125. Angled transition portion 125 forms a transition between relatively flat portion 127 at first end 148 (connected to cinching portion 132) and relatively flat portion 129 connected and adjacent to second end 116 of primary support portion 102. Guiding-ramp portion 124 at its angled transition portion 125 creates a ramp-angle $\alpha$ with lengthwise axis $A_L$. A longer distance D decreases ramp-angle $\alpha$, while a shorter distance D increases ramp-angle $\alpha$. A ramp-angle $\alpha$ that is relatively small may ease or smooth movement of first end 112 as it slides along guiding ramp portion 124, and particularly angled transition portion 125, and over second end 116, as described further below. In an embodiment, ramp-angle $\alpha$ is in a range of 10° to 60°; in another embodiment, ramp-angle $\alpha$ is in a range of 15° to 45°; in yet another embodiment, ramp-angle $\alpha$ is in a range of 20° to 40°.

Buckle or fastener assembly 106, in an embodiment, includes frame 154, rotatable cylinder 156 and sliding pin 158.

In an embodiment, and as depicted, frame 154 generally forms a rectangular shape, and includes first (left) member 160, second member (right) 162, third member (top) 164 and fourth member (bottom) 166, the four members defining central opening 168. Frame 154 and its members may comprise a relatively rigid material, such as a metal, including steel, or plastic.

Rotatable cylinder 156 is fit loosely over first member 160 and comprises a cylinder having a length similar to a length of first member 160.

Sliding pin 158 extends from a point above third member 164 past fourth member 166 through central opening 168. Sliding pin 158 defines a first or top hole which receives third member 164 and a second or bottom hole with receives fourth member 166. An inside diameter of the first and second holes may be slightly larger than an outside diameter of frame members 164 and 166, such that sliding pin 158 is configured to move or slide to various positions between third member 164 and further member 166. In an embodiment, sliding pin 158 may have a knurled surface to improve a grip with strap portion 104.

Second member 162 is received into sleeve 150 of first end portion 138 of strap portion 104, thereby connecting buckle 106 to primary support portion 102 and lifting belt 100.

Figure 3:
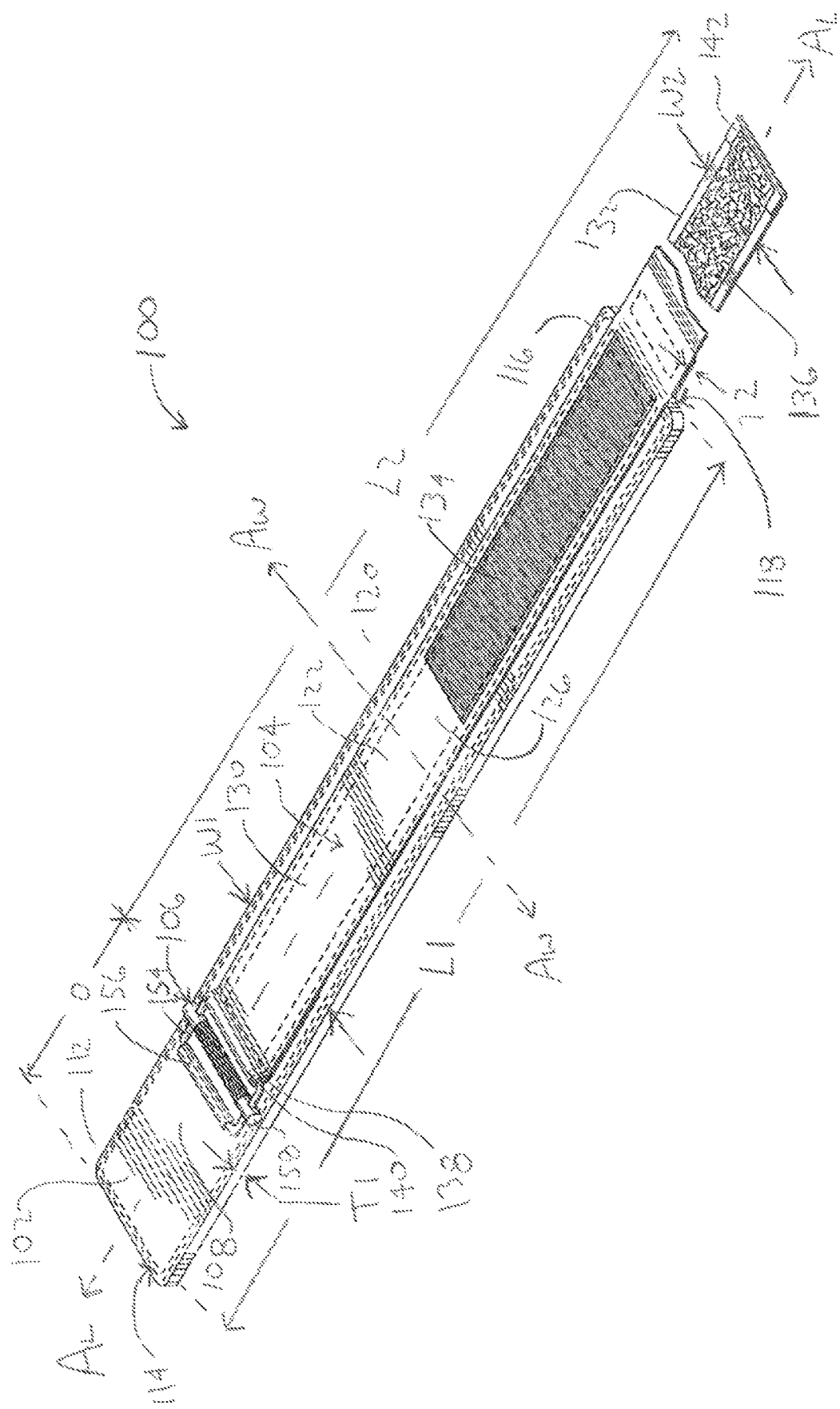
FIG. 3 is a perspective view of the lifting belt of FIG. 1 in an unbuckled configuration, according to an embodiment of the disclosure.
Figure 4:
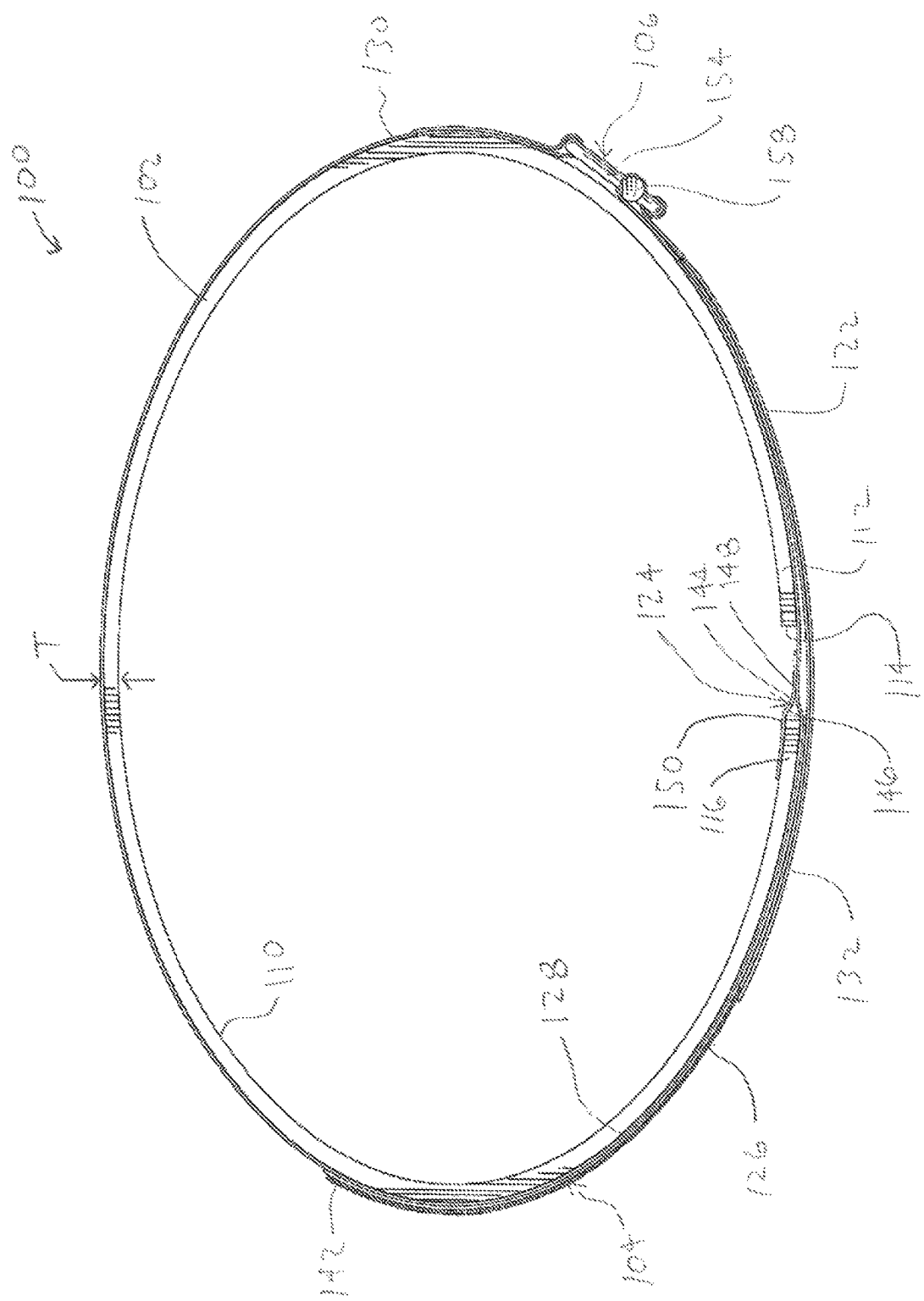
FIG. 4 is a top view of the lifting belt of FIG. 1 in the first buckled configuration, according to an embodiment of the disclosure.
Figure 5:
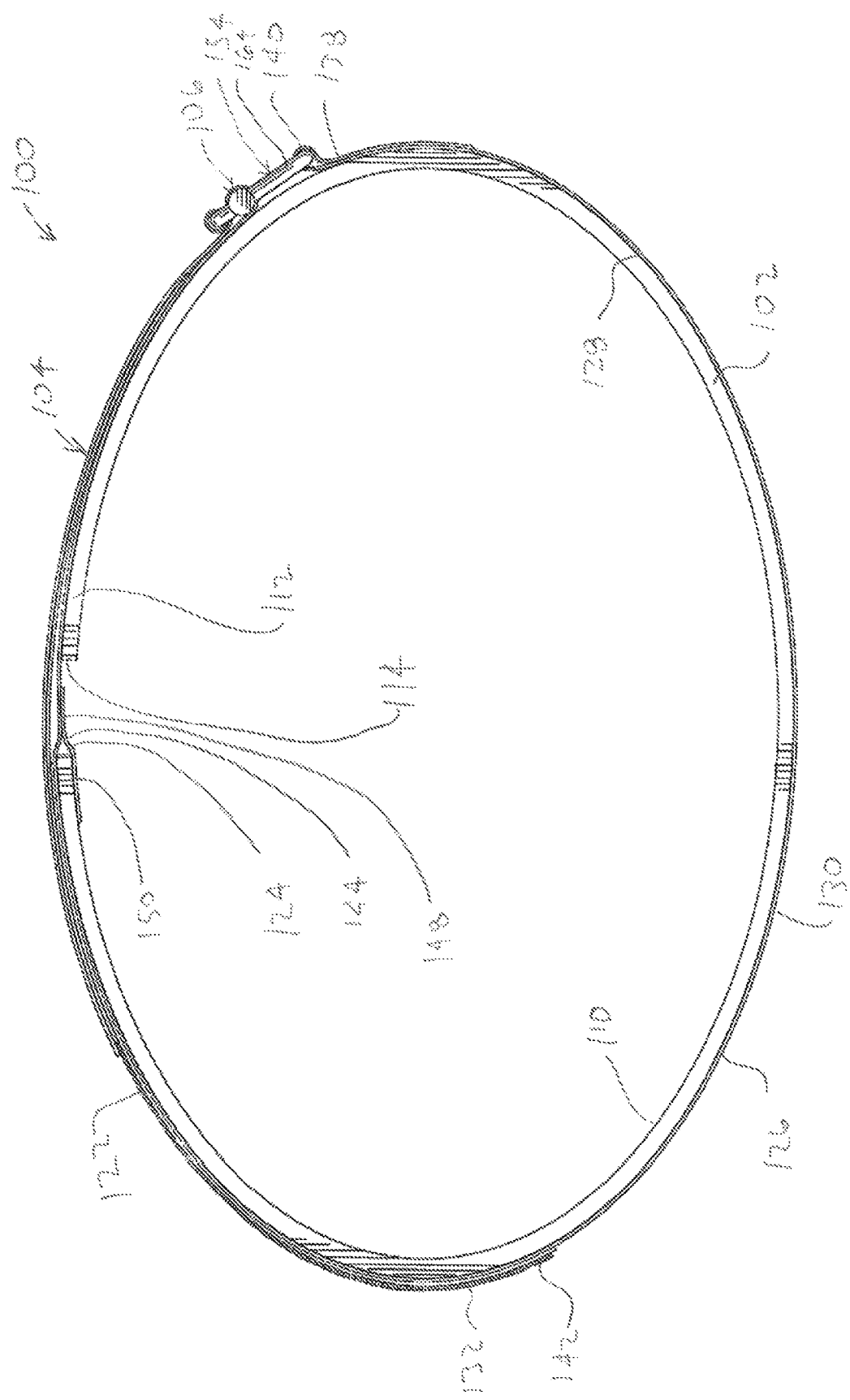
FIG. 5 is a bottom view of the lifting belt of FIG. 1 in the first buckled configuration, according to an embodiment of the disclosure.
Figure 6:
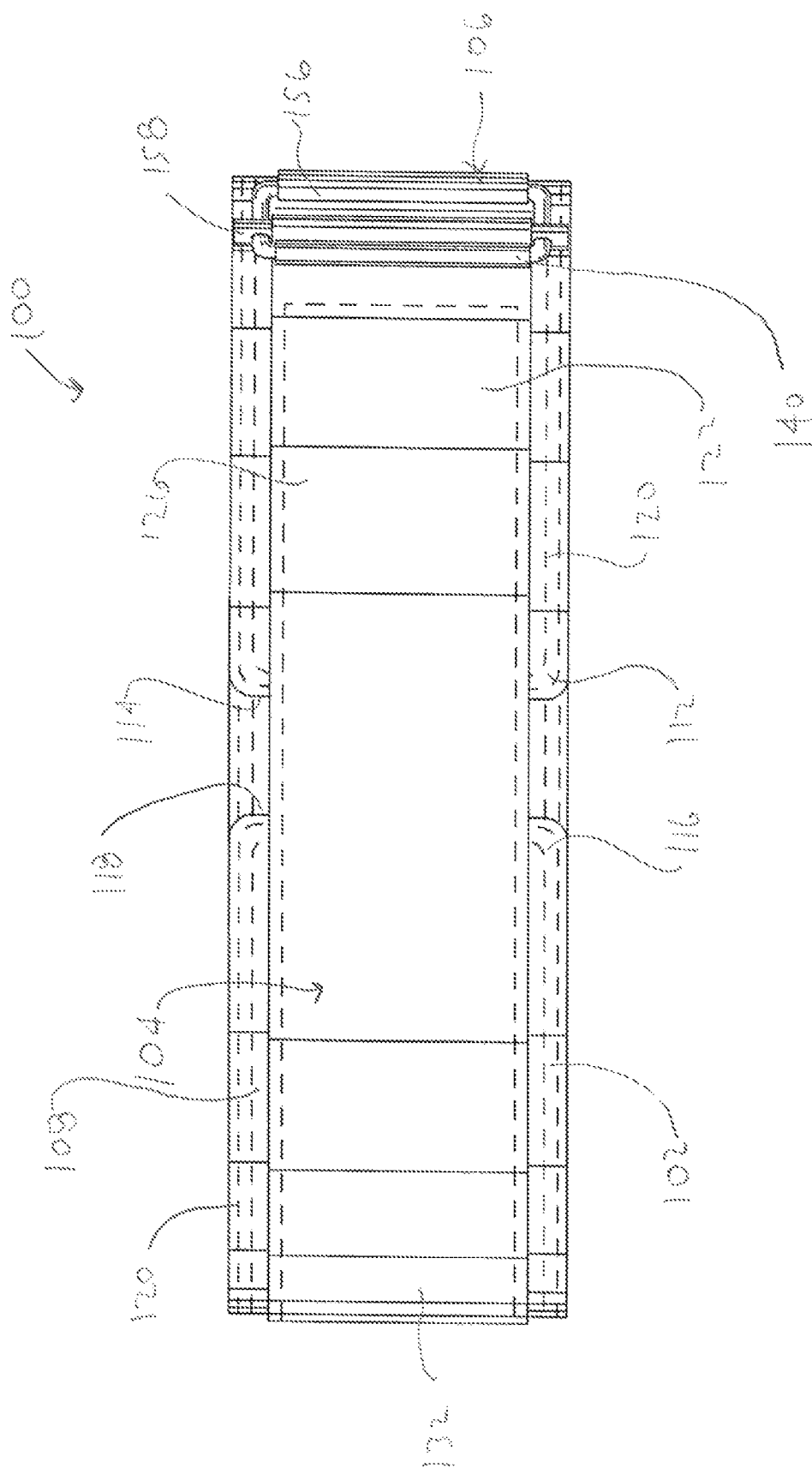
FIG. 6 is a front view of the lifting belt of FIG. 1 in the first buckled configuration, according to an embodiment of the disclosure.
Figure 7:
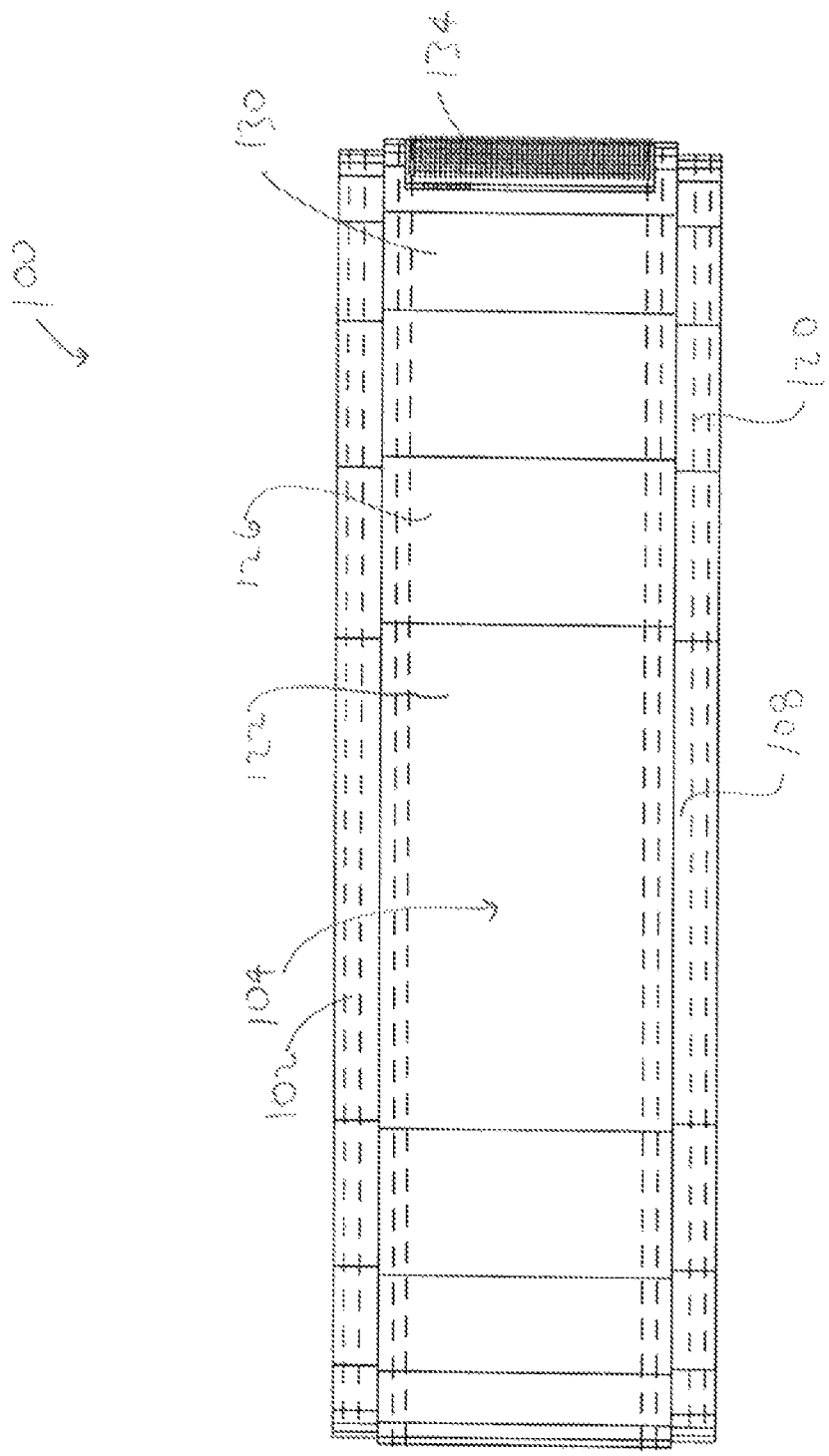
FIG. 7 is a rear view of the lifting belt of FIG. 1 in the first buckled configuration, according to an embodiment of the disclosure.
Figure 8:
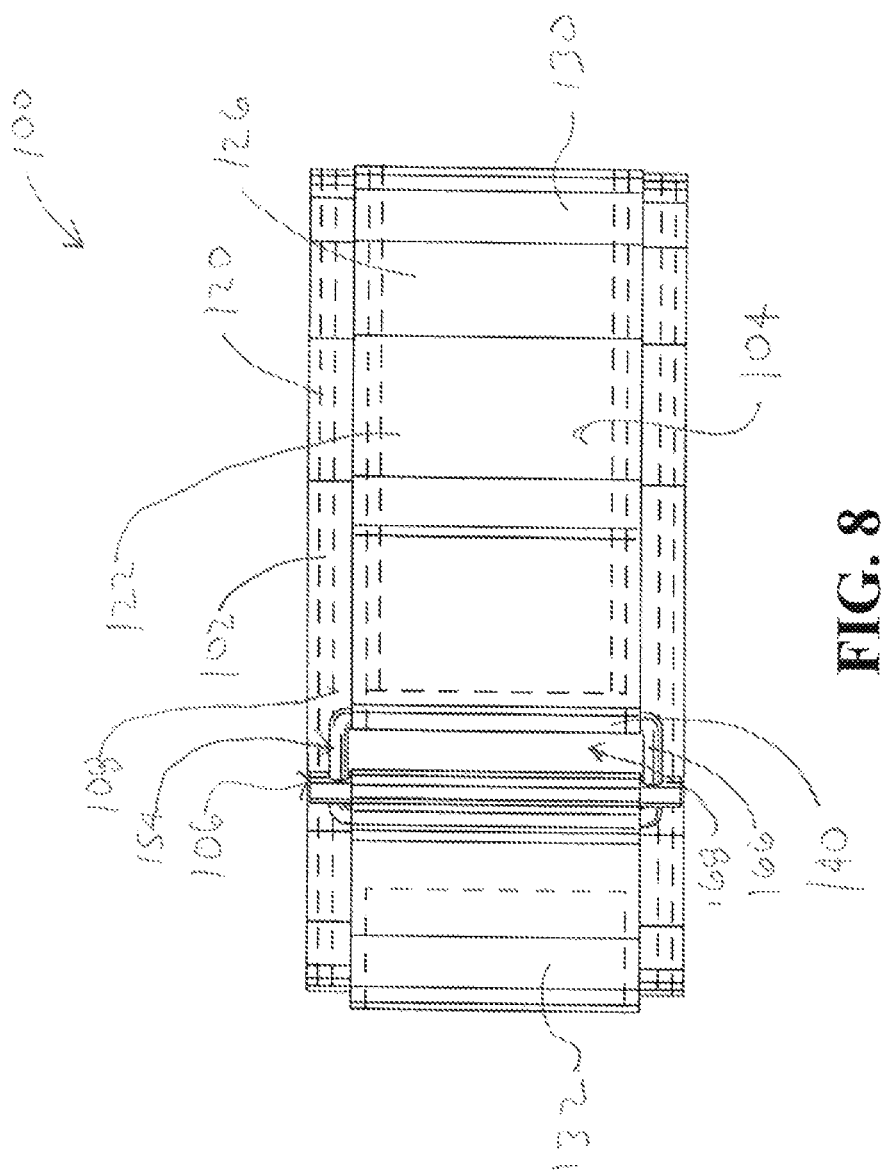
FIG. 8 is a right-side view of the lifting belt of FIG. 1 in the first buckled configuration, according to an embodiment of the disclosure.
Figure 9:
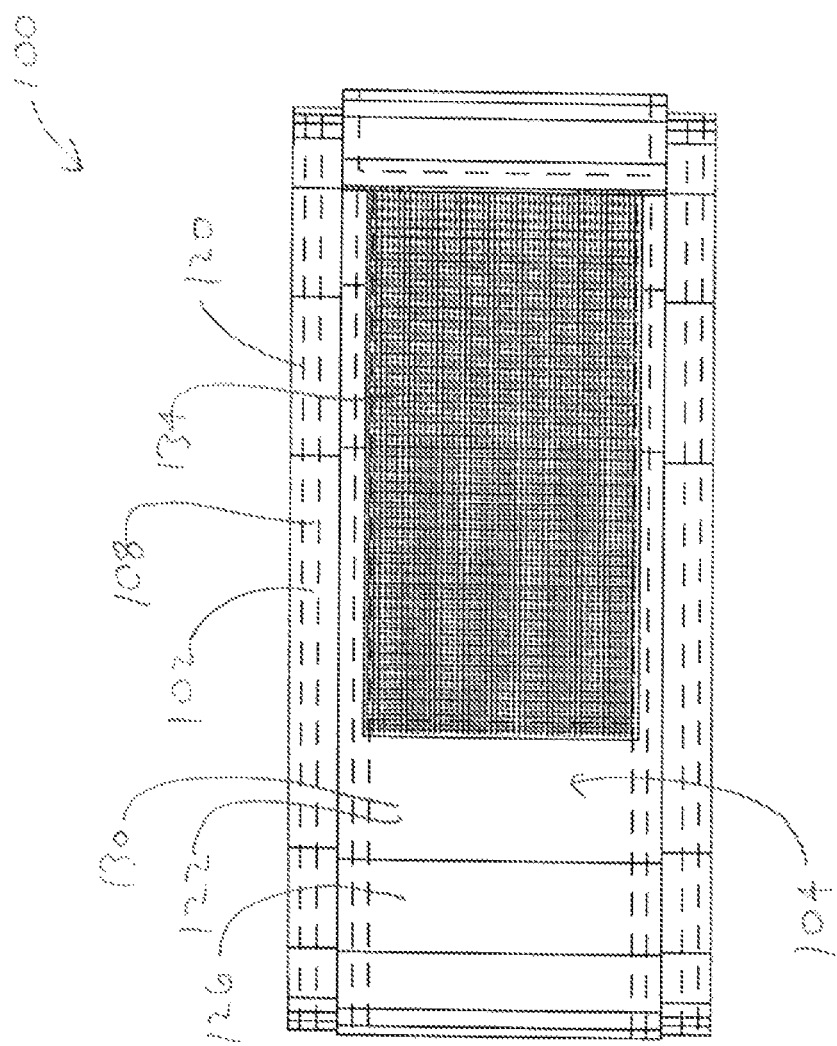
FIG. 9 is a rear view of the lifting belt of FIG. 1 in the first buckled configuration, according to an embodiment of the disclosure.

Referring specifically to FIG. 3, lifting belt 100 is depicted in an unbuckled or unfastened configuration. In contrast, FIGS. 1 and 10 depict lifting belt 100 in first and second buckled and fastened positions, respectively.

Referring to both FIGS. 1 and 10, in the buckled and fastened positions, cinching portion 132 of strap portion 104 is engaged with buckle assembly 106 such that cinching portion 132 is wrapped around sliding pin 158 and is between rotating cylinder 156 and sliding pin 158. Cinching portion 132 is folded over on itself such that hook portion 134 engages with loop portion 136 (see also FIG. 3 for hook and loop portions), thereby causing lifting belt 100 to be in a buckled and fastened position. In these first and second buckled and fastened configurations, lifting belt 100 forms a loop, the first loop of the first configuration being somewhat larger than the second loop of the second configuration.

Referring specifically to FIG. 1, in this first configuration, first end 112 of primary support portion 102 is located some distance away from second end 114 of primary support portion 102, such that the loop or oval shape formed by lifting belt 100 is relatively large. In this first configuration, primary support portion 102 does not overlap itself. In other words, second end 116 of primary support portion 102 is not positioned over and adjacent to first end 112.

In contrast, and referring to FIG. 10, portions of primary support portion 102 are overlapping. More specifically, second end 112 of primary support portion is positioned adjacent to second end 114, such that first end 112 is positioned closer to an interior of the loop formed by lifting belt 100, which when in use, is closer to a user's torso. Such an overlap may be necessary in order for lifting belt 100 to be adequately tight against the user's torso and provide the desired pressure and support to the user's torso.

To fit and adjust lifting belt 100, a user firstly wraps lifting belt 100 around the user's torso, placing inner side 110 of primary support portion 102 against the torso. Next, the user threads second end 142 of cinching portion 132 of strap portion 104 through central opening 168 of buckle frame 106, between sliding pin 158 and second frame member 162, over sliding pin 158, and back through the space between sliding pin 168 and rotating cylinder 156. The user then pulls on cinching portion 132 causing first end 112 and second end 116 of primary support portion 102 to move towards one another, and to tighten lifting belt 100 around the torso.

Cinching portion 132 is then folded against attached portion 130 (see also FIG. 3), such that hook portion 134 on attached portion 130 of strap 104 is engaged with loop portion 136 on cinching portion 132, thereby completing the fastening process.

Depending on the length of cinching portion 132 pulled through buckle assembly 106, first end 112 and second end 114 of primary support portion 102 may overlap. In known leather lifting belts, the relatively thick ends of the leather belt may be moved together and initially abut one another, obstructing passage of one end over the other end, and interfering with fitment, which could not only lead to user discomfort, but to a lack of sufficient support. The guiding ramp 124 feature of lifting belt 100 avoids such interference and subsequent problems for the user.

Referring to FIGS. 11-15, lifting belt 100 is depicted in multiple adjustment stages, with guiding-ramp portion 124 and its angled transition portion 125 guiding ends 112 and 114 of primary support portion 102 from a separated position, such as depicted also in FIG. 10, around each other into an overlapping position such as depicted in FIG. 11.

Referring specifically to FIG. 11, a view depicting inner side 110 (the side to be fit against the user's torso) of primary support portion 102, with attached ramp portion 124, and depicting a segment of cinching portion 132 attached to guiding-ramp portion 124 and to outer side 108 (see FIG. 3). Inner side 144 of guiding-ramp portion 124 faces the same direction as inner side 108 of primary support portion 102, and as explained further below with respect to FIGS. 12-15, guides first end 112 of primary support portion 102 with its first end face 114 (see also FIGS. 1 and 10) over second end 116 and its end face 118.

Figure 13:
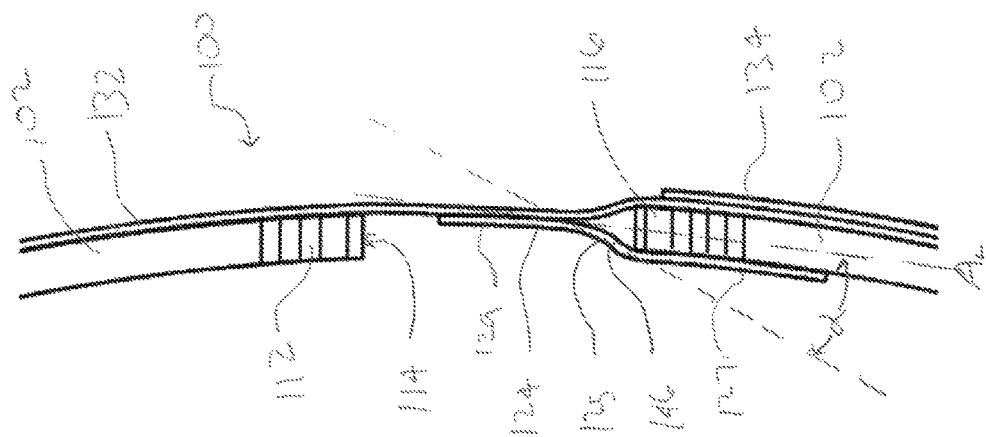
FIG. 13 is a top view of ends of the lifting belt, according to an embodiment of the disclosure.
Figure 12:
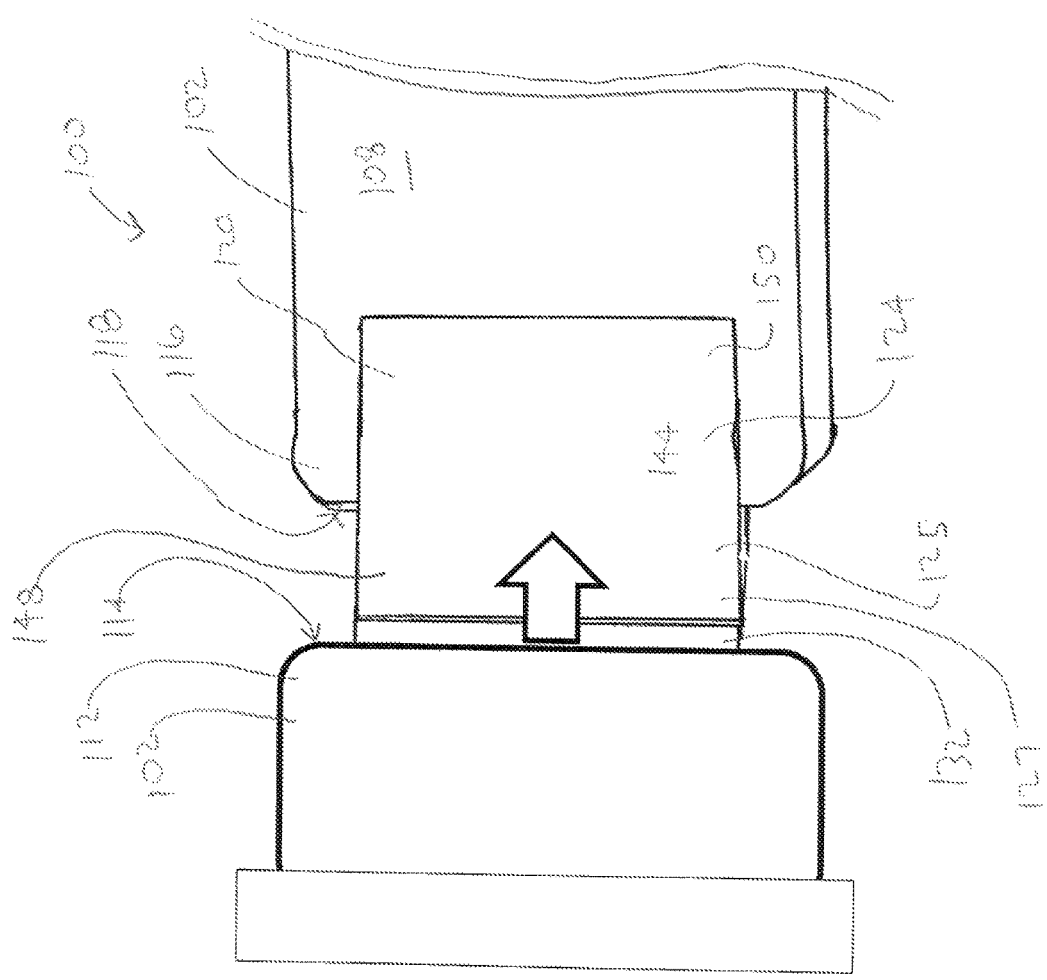
FIG. 12 is a view of an inner side of the lifting belt depicting two ends moving towards each other.

Referring to FIGS. 12 and 13, first end 112 with end face 114 has been or is being advanced in the direction of the depicted arrow (FIG. 12) toward second end 116 by pulling on cinching portion 132 of strap portion 104, also in the direction of the depicted arrow, after cinching portion 132 has been threaded through buckle assembly 106 (see also FIGS. 1 and 10). Although it is described that first end 112 is moved toward second end 116, it will be understood that second end 116 may be moved toward first end 112, or that both first end 112 and second end 116 move toward each other. In other words, when cinching belt 132 is threaded through the buckle assembly 106 then pulled, there is a relative movement of one or both ends 112, 116 causing the ends to be closer to one another when the longitudinal pulling force is applied. First end 112 moves generally or substantially along lengthwise axis $A_L$ towards second end 116 when cinching portion 132 is pulled.

In the embodiment depicted, and as described briefly above, angled transition portion 125 of guiding-ramp portion 124 forms an angle α with respect to lengthwise axis $A_L$. In this depiction, first end 112 of primary support portion 102 is approaching, but has not yet reached, guiding-ramp portion 124 and its angled transition portion 125.

Figure 15:
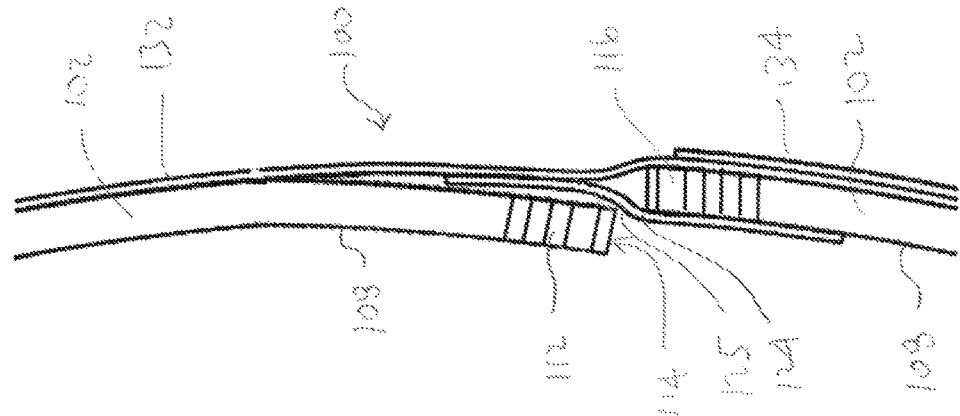
FIG. 15 is a top view of an end of the primary support portion engaging a guiding ramp portion, according to an embodiment of the disclosure.

Referring to FIGS. 14 and 15, first end 112 of primary support portion 102 has been pulled by cinching portion 132 of strap portion 104 such that first end 112 with first end face 114 is over and adjacent to portion 127 of guiding-ramp portion 124 and is in contact with angled transition portion 125 at inner side 144 of guiding-ramp portion 124. As cinching portion 132 is pulled, first end 112 with first end face 114 and guiding-ramp portion 124 move relative to each other, such that first end 112 slides along inner side 144 of guiding-ramp portion 124, including along angled transition portion 125, and over second end 116, to a final position as depicted in FIG. 10. As such, guiding-ramp portion 124 prevents first end 112 from colliding with second end 116, and particularly, first end face 114 from colliding with second end face 118, when cinching portion 132 is pulled and lifting belt 100 is fitted to the user's torso.

In contrast, known lifting belts when the lifting belt is tightened, the end faces interfere, resulting in inconvenience, discomfort and potentially, poor fitment, as mentioned above. This is particularly true for known lifting belts with relatively thick support portions, such as thick leather support portions.

Embodiments of lifting belt 100 with guiding-ramp portion 124 avoid this interference issue and resulting negative outcomes.

Method steps of using lifting belt 100 are described above with respect to the figures. A method of using lifting belt 100 with guiding-ramp 100 include:

Placing or wrapping lifting belt 100 on the torso of a user such that an inner side 110 of a primary support portion 102 of lifting belt 100 is adjacent to the torso, and such that primary support portion 102 forms an open loop shape;

Threading an end 142 of a cinching portion 132 of strap portion 104 through a buckle assembly 106, causing the cinching portion 132 to be folded over;

Pulling the end 142 of the cinching portion 132, causing first and second ends 112 and 114 of support portion 102 to move towards one another;

Pulling the end 142 of the cinching portion 132, causing the first end 112 to engage with a guiding ramp 124, then engagably slide along an inner side 144 of guiding-ramp 124 and its angled transition portion 125 until the first end 112 moves past second end 114, such that end portions of primary support portion 102 overlap; and Placing cinching portion 132 against an attached portion 130 of strap portion 104, causing a hook portion 134 to engage with a loop portion 136, thereby connecting the cinching portion 132 to the attached portion 130 and providing additional, secondary support.

All of the features disclosed in this specification (including the references incorporated by reference, including any accompanying claims, abstract and drawings), and/or all of the steps of any method or process so disclosed, may be combined in any combination, except combinations where at least some of such features and/or steps are mutually exclusive.

Each feature disclosed in this specification (including references incorporated by reference, any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any incorporated by reference references, any accompanying claims, abstract and drawings), or to any novel one, or any novel combination, of the steps of any method or process so disclosed The above references in all sections of this application are herein incorporated by references in their entirety for all purposes.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents, as well as the following illustrative aspects. The above described aspects embodiments of the invention are merely descriptive of its principles and are not to be considered limiting. Further modifications of the invention herein disclosed will occur to those skilled in the respective arts and all such modifications are deemed to be within the scope of the invention.

DISCLOSURE ELEMENT LIST

100 Lifting belt
102 Primary support portion
104 Strap portion
106 Buckle or fastener
108 First, front or outer side
110 Second, back or inner side
112 First end of primary support portion 102
114 First end face 114 of first end 112
116 Second end of primary support portion 102
118 Second end face of second end 116
120 Optional decorative stitching
122 First or main portion of strap portion 104
124 Guiding-ramp portion of strap portion 104
125 Angled transition portion of guiding-ramp portion 124
126 First, outer or top side
127 First flat portion of guiding-ramp portion 125
128 Second, inner or bottom side
129 Second flat portion of guiding-ramp portion 125
130 Attached portion of main portion 122 of strap portion 104
132 Extending or cinching portion of main portion 122 of strap portion 104
134 Optional hook portion
136 Optional loop portion
138 First end portion of attached overlapping portion 130
140 Sleeve or channel of first end portion 138
142 Second end of cinching portion 132
144 First or inner side of guiding-ramp portion 124
146 Second or outer side of guiding-ramp portion 124
148 First end of guiding-ramp portion 124
150 Second end of guiding-ramp portion 124
152 Point of attachment
154 Frame of buckle 106
156 Rotatable cylinder
158 Sliding pin
160 First (left) member
162 Second member (right)
164 Third member (top)
166 Fourth member (bottom)
168 Central opening
L1 Length of primary support portion 102
W1 Width of primary support portion 102
T1 Thickness of primary support portion
L2 Length of main portion 122 of strap portion 104
W2 Width of main portion 122 of strap portion 104
T2 Thickness of main portion 122 of strap portion 104.

What is claimed is:

1. A lifting belt for fitment on a torso of a user, comprising:
a primary support portion defining a first width and a first thickness, and including a first end with a first end face, a second end with a second end face, an inner side and an outer side;
a fastening assembly connected to the primary support portion; and
a strap portion including:
a main portion having an attached portion attached to the primary support portion and a cinching portion configured to engage with the fastening assembly for securing and adjusting fitment of the lifting belt, the cinching portion connected to the primary support portion and extending from the second end of the primary support portion, the cinching portion defining a second width and a second thickness; and
a guiding ramp portion having a first end connected to the cinching portion and a second end connected to the inner side of the primary support portion, thereby forming a guiding ramp between the inner side of the cinching strap portion and the inner side of the primary support portion such that the first end is guided along the guiding ramp portion and over the second end when the lifting belt is fitted to the torso of the user.

2. The lifting belt of claim 1, wherein the guiding ramp portion forms an angled transition portion.

3. The lifting belt of claim 2, wherein the angled transition portion forms an angle with a lengthwise axis of the primary support portion in a range of 10° to 60° when the guiding ramp portion is subjected to a pulling force along the lengthwise axis.

4. The lifting belt of claim 3, wherein the angle is in a range of 15° to 45°.

5. The lifting belt of claim 1, wherein the primary support portion comprises a leather material, and the cinching portion of the strap portion comprises a nylon material, and the first thickness of the primary support portion is greater than the second thickness of the cinching portion.

6. The lifting belt of claim 1, wherein the guiding ramp portion defines a third width that is less than the first width of the primary support portion.

7. The lifting belt of claim 6, wherein the third width of the guiding ramp portion is substantially the same as the second width of the cinching portion.

8. The lifting belt of claim 1, wherein an end face width of the first end face is substantially equal to the first thickness of the primary support portion and is greater than the second thickness of the cinching portion.

9. The lifting belt of claim 8, wherein the primary support portion comprises leather, the cinching portion and the guiding ramp portion comprise a polymer material, the cinching portion is sewn to the outer side of the primary support portion at the second end and the guiding ramp portion is sewn to the inner side of the primary support portion.

10. The lifting belt of claim 1, further comprising a hook portion on an attached portion of the strap portion facing outwardly from the outer side of the primary support portion and a loop portion configured to engage with the hook portion, the loop portion attached to an end of the cinching portion.

11. The lifting belt of claim 1, wherein the fastening assembly comprises a buckle assembly with a buckle frame, sliding pin and rotating cylinder.

12. A method of fitting the lifting belt of claim 1 onto a torso of a user, comprising the steps of:
wrapping the lifting belt around the torso of the user such that the inner side of the primary support portion is adjacent to the torso, causing the primary support portion to form a loop shape;
threading an end of the cinching portion through the fastening assembly;

pulling the end of the cinching portion, causing the first and second ends of the support portion to move towards one another;

pulling the end of the cinching portion, causing the first end to engage with the guiding ramp portion, and to engagably slide along an inner side of the guiding ramp portion until the first end moves past the second end, such that the first end face and the second end face do not contact one another, and end portions of the primary support portion overlap.

13. The method of claim 12, further comprising placing the cinching portion against an attached portion of the strap portion, causing a hook portion on the primary support portion to engage with a loop portion on the cinching portion of the strap portion, thereby connecting the cinching portion to the attached portion and the primary support portion.

14. A lifting belt for fitment on a torso of a user, comprising:
  a leather primary support portion defining a first width and first thickness and including a first end with a first end face defining a first end-face width, a second end with a second end face, an inner side and an outer side, the first thickness being in a range of 2 mm to 12 mm and the first end-face width being in a range of 2 mm to 12 mm;
  a buckle assembly connected to the primary support portion; and
  a strap portion including:
    a main portion having an attached portion attached to the primary support portion and a non-leather cinching portion configured to engage with the buckle for securing and adjusting fitment of the lifting belt, the non-leather cinching portion sewn to the outer side of the leather primary support portion and extending from the second end of the leather primary support portion, the non-leather cinching portion defining a second width that is less than the first width of the leather primary support portion, and a second thickness that is less than the first thickness of the leather primary support portion; and
    a guiding ramp portion having a first end connected to the cinching portion and a second end sewn to the inner side of the leather primary support portion, thereby forming a guiding ramp between the inner side of the non-leather cinching strap portion and the inner side of the leather primary support portion such that the first end of the leather primary support portion is guided along the guiding ramp portion and over the second end of the non-leather primary support portion when the lifting belt is fitted to the torso of the user.

15. The lifting belt of claim 14, wherein the guiding ramp portion forms an angled transition portion.

16. The lifting belt of claim 15, wherein the guiding ramp portion forms an angle with a lengthwise axis of the leather primary support portion in a range of 10° to 60° when the guiding ramp portion is subjected to a pulling force along the lengthwise axis.

17. The lifting belt of claim 16, wherein the non-leather cinching portion comprises a nylon cinching portion and the guiding ramp portion comprises a nylon material.

18. The lifting belt of claim 14, wherein a length of the guiding ramp portion is greater than the first thickness of the leather primary support portion and less than a length of the cinching portion.

19. The lifting belt of claim 14, wherein a width of the guiding ramp portion is less than the second width of the leather primary support portion.

* * * * *